United States Patent
Yasumoto

(10) Patent No.: US 6,794,885 B1
(45) Date of Patent: Sep. 21, 2004

(54) DEVICE FOR INSPECTING HERMETICALLY SEALED PACKAGES

(75) Inventor: Kenji Yasumoto, Toyonaka (JP)

(73) Assignee: Joven Denki Kabushiki Kaisha, Osaka (JP)

( * ) Notice: Subject to any disclaimer, the term of this patent is extended or adjusted under 35 U.S.C. 154(b) by 0 days.

(21) Appl. No.: 10/148,915

(22) PCT Filed: Nov. 24, 2000

(86) PCT No.: PCT/JP00/08319

§ 371 (c)(1), (2), (4) Date: May 31, 2002

(87) PCT Pub. No.: WO01/40057

PCT Pub. Date: Jun. 7, 2001

(30) Foreign Application Priority Data

Dec. 3, 1999 (JP) .......................... 11-344116

(51) Int. Cl.[7] .............................................. G01N 27/00
(52) U.S. Cl. ..................................................... 324/557
(58) Field of Search ................................ 324/557, 558; 73/52, 40, 49.2, 49.3

(56) References Cited

U.S. PATENT DOCUMENTS 4,914,395 A * 4/1990 Hamada ...................... 324/557

6,288,554 B1 * 9/2001 Yasumoto ................... 324/558

FOREIGN PATENT DOCUMENTS

JP         H9-222378        8/1997

* cited by examiner

*Primary Examiner*—N. Le
*Assistant Examiner*—Amy He
(74) *Attorney, Agent, or Firm*—Koda & Androlia

(57) ABSTRACT

While a sealed package (3) prepared by wrapping conductive contents (1) with an electric-insulation film (2) is being conveyed by two conveyors (4, 4), front and rear, a conductor (5) disposed on one side of a conveyance path (A) and at least one of two conductors (6, 6), front and rear, disposed on the other side are simultaneously contacted with opposed surfaces of the sealed package (3) being conveyed. In this state, a high voltage from a high voltage source (7) is applied to the sealed package (3), and a current detector (8) is used to detect whether or not a change in current is occurring in the portion which is in contact with the conductor (5) and the portion which is in contact with at least one of the two conductors (6, 6) so as to find pinholes in the sealed package (3). Whether or not there is a pinhole in at least one of the opposed surfaces in the portion of the sealed package (3) where the contents (1) exist can be detected by simultaneous inspection from both surfaces. Pinhole inspection can be effected by increasing the applied voltage.

2 Claims, 2 Drawing Sheets

(a)

(b)

(c)

(d)

DEVICE FOR INSPECTING HERMETICALLY SEALED PACKAGES

TECHNICAL FIELD

The present invention relates to a method and a device for detecting pinholes on hermetically sealed packages, which wrap, with an electric insulating film, conductive contents, e.g, medical consumable products such as blood products and normal saline solutions, as well as foods, etc.

BACKGROUND ART

Hermetically sealed packages are used in a variety of products today to maintain the sterilized condition of the contents of these products. These products include a number of products, for example, a variety of medical consumable products such as blood for transfusion and blood products, as well as food products such as retort foods.

It is extremely important to inspect these hermetically sealed packages for pinholes. A pinhole in the package of a medical consumable product causes contamination or decomposition of the contents. A pinhole in the package of a food product causes the contents to contact the atmosphere, leading to decomposition or decay of the contents.

In a conventional method for detecting pinholes, for example, that described in Japanese (Examined) Patent Application Publication S50-6998 (1975), a subject, which is a packaged item, is placed between a pair of electrodes. When a voltage is applied to these electrodes while substantially differentiating the electrostatic capacity formed between one electrode and the subject and the electrostatic capacity formed between the other electrode and the subject, a spark is produced between one electrode and the subject, causing an electric current. The existence of a pinhole can be detected when the electric current is detected.

In the above method, in which the existence of a pinhole is detected by detecting the electric current caused by the spark, the existence of a pinhole is actually detected by the variation in the strength of the detected current (whether it becomes stronger or weaker).

In this case, when a voltage is applied to the two electrodes that hold a hermetically sealed package between them, either a leakage current or a charging current always flows regardless of the existence of a pinhole. Such a current becomes stronger as the voltage becomes higher. The current is also affected by the climate, for example, the humidity and temperature of the periphery of the subject, which form the atmosphere at the time of the inspection. The leakage current, for example, becomes stronger when it rains or when the humidity is high. Fine floating dust also affects the electric current at the detector. When checking the existence of a pinhole by the magnitude of the electric current running in a short period of time, the detector sometimes concludes that there is a pinhole even if there is no pinhole. In this method, malfunctions are inevitable.

Moreover, when a high voltage is applied to the two electrodes holding a hermetically sealed package between them, an electric potential difference concentrates on the weak portion of the electric insulating film of the hermetically sealed package, providing a cause for pinholes. As a result, there will be more pinholes, adversely affecting the subject.

In order to solve these problems, the applicant invented a method (Japanese Pat. No. 2908751, etc.) in which a hermetically sealed package is installed on a supporting electrode that is grounded, a high direct current voltage is applied between the supporting electrode and yet another electrode that contacts or approaches the test portion of the hermetically sealed package in close proximity, and the electrode that contacts the test portion is grounded while the ground of the supporting electrode is disengaged or kept engaged, thereby detecting a discharge current from the test portion to inspect the hermetically sealed package for pinholes.

According to this method, the existence of a pinhole on a hermetically sealed package can be checked efficiently, but the method still requires a series of inspection procedure. In a further exploration for an easier procedure, the applicant developed a technology that does not require the supporting electrode that contacts the side surface of the hermetically sealed package (Japanese Patent Application H10-211868 (1998), Japanese Patent Application H11-16597 (1999)).

In this method, an electrode is placed so as to contact or approach the test portion of the hermetically sealed package in close proximity, and a high voltage is applied between the test portion of the hermetically sealed package and the supporting electrode that supports the hermetically sealed package. In the previously mentioned method in which the existence of a pinhole is detected by detecting the current generated by a spark, a high voltage is applied between the electrodes that hold the hermetically sealed package. In either method, while it is possible to check whether or not there are pinholes on the surface of the test portion of the hermetically sealed package that the supporting electrode contacts, it is impossible to check whether or not there are pinholes on the two, relatively wide, opposing surfaces of the hermetically sealed package in simultaneous inspections of the both surfaces.

During the course of further explorations and experiments for a better method of inspection that replaces the above method, the applicant discovered that when a high voltage is applied to a hermetically sealed package having relatively flat surfaces through its two opposing surfaces, it is possible to check whether or not there are pinholes on at least one of the relatively flat opposing surfaces of the hermetically sealed package in simultaneous inspections from the both surfaces. This discovery has led to the present invention.

The present invention is extremely effective when it is applied to hermetically sealed packages having flat surfaces, in particular, those containing such contents as medical consumable products including blood products, e.g., blood for transfusion, plasma, etc., as well as foods, etc., including retort foods. The present invention can also be applied to packages that do not have flat surfaces, for example, those having circular arc surfaces, as long as the conductive elements of the present invention can contact relatively wide areas of the exterior circular arc surfaces.

DISCLOSURE OF INVENTION

According to the inspection method of the present invention, while a hermetically sealed package 3, which wraps, with an electric insulating film 2, conductive contents 1, e.g., blood for transfusion, blood products, etc., is conveyed, a conductive element 5 arranged on one side of the package's path A and at least one of the two longitudinally arranged conductive elements 6, 6 arranged on the other side are made to simultaneously contact the opposing surfaces of the contents 1—existing portion of the hermetically sealed package 3. In this condition, a high voltage is applied to the hermetically sealed package 3 to detect a change in the electric current at the portion where the conductive element 5 contacts or the portion where at least one of the two conductive elements 6, 6 contacts, thereby detecting a pinhole on the hermetically sealed package 3.

Using this method, the conductive element 5 arranged on one side of the path A and at least one of the two longitudinally arranged conductive elements 6, 6 arranged on the other side contact the portions of the opposing surfaces of the contents 1—existing portion of the hermetically sealed package 3. In this condition, a high voltage is applied to the hermetically sealed package 3 to detect a change in the electric current at the portion where the conductive element 5 contacts or the portion where at least one of the two conductive elements 6, 6 contacts, thereby checking the existence of a pinhole on at least one of the portions on the opposing surfaces of the contents 1—existing portion of the hermetically sealed package 3 in simultaneous inspections of both surfaces.

According to the inspection device of the present invention, two conveyors 4, 4 for conveying the hermetically sealed package 3, which wraps, with an electric insulating film 2, conductive contents 1, e.g., blood for transfusion, blood products, etc., are arranged longitudinally with an interval between them that is sufficiently small for the hermetically sealed package 3 to be handed over from one to the other. The conductive element 5 approaches the path A from one side of the space between the two conveyors 4,4 and the two conductive elements 6, 6 approach the path A from the other side of the path A. At this time, these conductive elements are longitudinally separated from each other for such distances that make it possible for the conductive element 5 and at least one of the two conductive elements 6, 6 to contact the opposing surfaces of the contents 1—existing portion of the hermetically sealed package 3 from both sides of the path A simultaneously as the package is conveyed. A high-tension power unit 7 is connected to either the conductive element 5 or the two longitudinally arrange conductive elements 6,6, which approach the path A from each respective side. An electric current detector 8 for detecting an electric current change at the portion where the conductive element 5 contacts and the portion where at least one of the two longitudinally arranged conductive elements 6,6 contacts is connected to the other.

Using this device, the hermetically sealed package 3 can be conveyed by the operation of the two longitudinally conveyors 4, 4. From both sides of the path A, the conductive element 5 arranged on one side of the path A and at least one of the two longitudinally arranged conductive elements 6, 6 arranged on the other side, simultaneously contact the opposing surfaces of the contents 1—existing portion of the hermetically sealed package 3 that is moving on the path A. In this condition, a high voltage is applied to the hermetically sealed package 3 from the high-tension power unit 7. If a change in the electric current is detected by the electric current detector 8 at the portion where the conductive element 5 contacts and the portion where at least one of the two longitudinally arranged conductive elements 6, 6 contacts, it is concluded that at least one of the opposing surfaces of the contents 1—existing portion of the hermetically sealed package 3 has a pinhole. In this way, it is possible to inspect the entire areas of the opposing surfaces of the contents 1—existing portion of a hermetically sealed package 3 simultaneously from both surfaces to check whether or not there is a pinhole on any portion of at least one of the opposing surfaces.

Specifically, in the condition in which the conductive element 5 arranged on one side of the path A and at least one of the two longitudinally arranged conductive elements 6, 6 arranged on the other side simultaneously contact the opposing surfaces of the contents 1—existing portion of the hermetically sealed package 3 being conveyed from both sides of the path A, a high voltage is applied to the hermetically sealed package 3 to check by the electric current detector 8 whether there is a change in the electric current at the portion where the conductive element 5 contacts and the portion where at least one of the two longitudinally arranged conductive elements 6,6 contacts.

If there is a pinhole on any portion of at least one of the opposing surfaces of the contents 1—existing portion of the hermetically sealed package 3 being conveyed, over the entire areas of the opposing surfaces, a change occurs in the electric current at the portion where the conductive element 5 contacts and the portion where at least one of the two longitudinally arranged conductive elements 6, 6 contacts. If the electric current detector 8 detects the change in the electric current, it is concluded that at least one of the opposing surfaces of the contents 1—existing portion of the hermetically sealed package 3 has a pinhole. In this way, it is possible to inspect the entire areas of the opposing surfaces of the contents 1—existing portion of a hermetically sealed package 3 simultaneously form both surfaces to check whether or not there is a pinhole on any portion of at least one of the opposing surfaces.

On the other hand, if there are no pinholes on any portion of the entire areas of the opposing surfaces of the contents 1—containing portion of the hermetically sealed package 3 being conveyed, no change occurs at the portion where the conductive element 5 contacts and the portion where at least one of the two longitudinally arranged conductive elements 6, 6 contacts, therefore, the electric current detector 8 does not detect any change in the electric current. In this way, it is possible to inspect the entire areas of the opposing surfaces of the contents 1—existing portion of the a hermetically sealed package 3 simultaneously from both surfaces to check whether or not there is a pinhole on any portion of at least one of the opposing surfaces.

In the present invention, the longitudinal distance between the two conductive elements 6, 6, which are on the opposite side of the path A from the conductive element 5, can be extended generously within the range in which either one of them and the conductive element 5 can simultaneously touch the opposing surfaces of the contents 1—existing portion of the hermetically sealed package 3 being carried. Accordingly, the conductive element 6 and the conductive element 5 can be separated as far as possible. As a result, it is possible to make it difficult to produce sparks between the conductive element 6 and the conductive element 5, raising the limit to which the applicable voltage can be increased without causing any problem to inspections for pinholes.

The inspection method described in claim 1 has the following advantages: it makes it possible to check whether there is a pinhole on at least one of the opposing surfaces of the contents-existing portion of a hermetically sealed package in simultaneous inspections of both surfaces; and it also makes it possible to increase the voltage applied.

The inspection device of the present invention has the following effect: it is possible to convey relatively flat hermetically sealed packages one after another, and while doing so, inspect the entire areas of the opposing surfaces of the contents 1—existing portion of a hermetically sealed package 3 simultaneously from both surfaces to check continuously, accurately and without an error whether or not there is a pinhole on any portion of at least one of the opposing surfaces.

CODES

Figure 1:
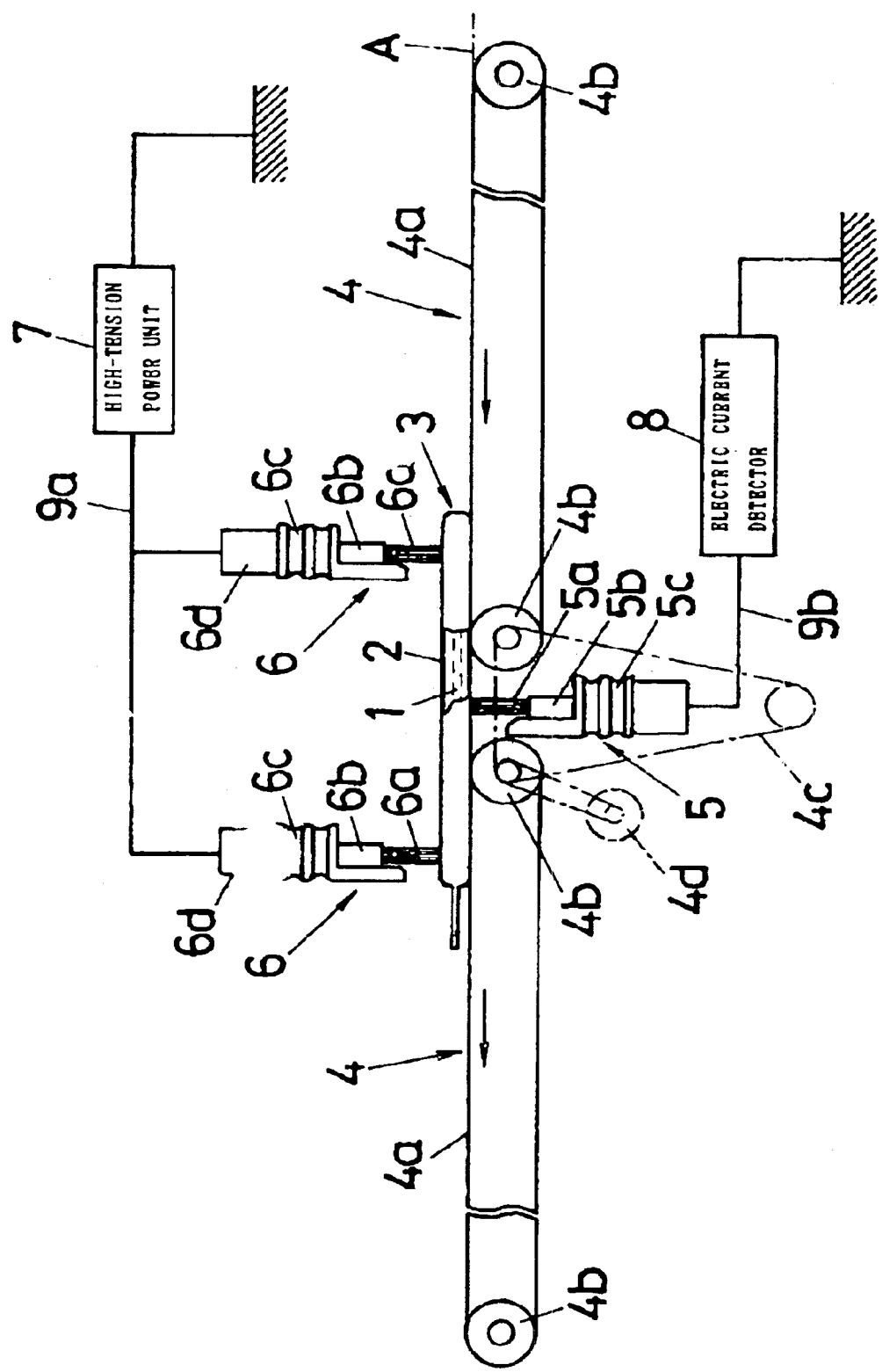
FIG. 1 is a schematic drawing of an example of a device for implementing the inspection method for hermetically sealed packages according to the present invention.

1: contents;
2: electric insulating film;
3: hermetically sealed package;
4: conveyor;
5,6: conductive elements;
5a, 6a: brushes;
7: high-tension power unit;
8: electric current detector;
A: path

BEST MODE FOR CARRYING OUT THE INVENTION

Preferred embodiments of the present invention will now be described by reference to the accompanying drawings.

The "conductive contents" concept according to the present invention includes not only substances clearly having conductivity, but also substances that can be charged with electricity, e.g., rice and purified water.

In the present invention, the electric insulating film 2 of the hermetically sealed package 3 for wrapping the conductive contents 1 is made of a plastic, a plastic film or glass.

If the contents 1 are blood products such as blood for transfusion and plasma, a flat plastic bag is used to hermetically seal such contents. Retort food wrapped in a laminated film can also take the form of a hermetically sealed package that is intended to be inspected using the present invention. In this case, a laminated film combining nylon and polypropylene, or polyester and polypropylene, or polyester, vinylidene chloride and polypropylene, is used as the electric insulating film 2.

When the present invention is applied to such hermetically sealed packages having flat surfaces as described above, it is possible to have the conductive element 5 and one of the two longitudinally arranged conductive elements 6, 6 contact the opposing surfaces of the contents 1—existing portion of a hermetically sealed package 3 simultaneously. In this way, it is easily examined whether there is a pinhole on at least one of the opposing flat surfaces of the contents 1—existing portion in simultaneous inspections of both surfaces.

On the other hand, if the contents 1 are a fish meat sausage, for example, a vinylidene chloride film bag is used. After filling the bag with ground fish meat, the ends of the bag are clipped with a wire and the bag is retorted and sterilized.

In this way, even if the hermetically sealed package 3 has circular arc surfaces, as long as the conductive elements 5, 6 arranged on the opposite sides of the path A can be made to touch relatively wide areas of the external surfaces of the circular arc, the present invention can be applied to such packages.

Special examples of the contents 1 include conductive fluids, e.g., conductive powder such as iron powder.

For the conductive element 5 and conductive elements 6, 6, which are arranged on the opposite sides of the path A, conductive brushes 5a, 6a can be used as shown in the drawings. The brushes 5a, 6a have a certain length and are planted on aluminium or SUS supporting members 5b, 6b respectively, which are further mounted on partially conductive supporting pedestals 5c, 6c.

The brushes 5a, 6a maybe made of metal fibres, metal-plated fibres, metal-deposited fibres or acrylic fibres. In order to insulate the supporting pedestals 5c, 6c, they can be made of tetrafluoroethylene resin, polycarbonate or reinforced polypropylene. In order to partially insulate the same, a conductor can be planted into each of the conductive supporting pedestals 5c, 6c. The brushes 5a, 6a need to have a length that makes it possible for them to touch the opposing surfaces of the contents 1—existing portion of the hermetically sealed package 3 for inspection. If the opposing surfaces are flat, the bristles need not be too long, but if the surfaces to be touched are circular arc, the brushes 5a, 6a need to have a sufficient length to reach the relatively wide areas of the surfaces.

Preferably, the brushes 5a, 6a, supporting members 5b, 6b and supporting pedestals 5c, 6c are designed to be wider than the width of the hermetically sealed package 3 for inspection so that the brushes 5a, 6a contact the entire widths of the opposing surfaces of the contents 1—existing portion of the hermetically sealed package 3 for inspection.

The two longitudinally arranged conveyors 4, 4 for conveying the hermetically sealed package 3 for inspection are endless, and they both run in the same direction at the same speed. They are both insulated and have a sufficient width to allow the hermetically sealed package 3 for inspection to be conveyed in a stable manner.

The two longitudinally arranged conveyors 4, 4 are arranged with a sufficient distance between them that allows the conductive element 5 to approach the path A from one side.

The conveyors 4, 4 should be designed to have such a length that allows the hermetically sealed packages 3 to be conveyed one after another without overlapping.

In order to apply a high voltage to the hermetically sealed package 3 being conveyed, either the conductive element 5 or the two longitudinally arranged conductive elements 6, 6, which approach the path A from both sides, are connected to a high-tension power unit 7 via a lead wire 9a. The other conductive element(s) is/are connected to an electric current detector 8 via a lead wire 9b. In this condition, a high voltage is applied to the hermetically sealed package 3 being conveyed, and the electric current detector 8 inspects whether there is a change in the electric current at the portion where the conductive element 5 contacts and the portion where at least one of the two longitudinally arranged conductive elements 6, 6 contacts. In this way, it is possible to inspect the entire areas of the opposing surfaces of the contents 1—existing portion of a hermetically sealed package 3 simultaneously from both surfaces to check whether or not there is a pinhole on any portion of at least one of the opposing surfaces.

In FIG. 1, the conductive elements 6, 6 are connected to the high-tension power unit 7 and the conductive element 5 is connected to the electric current detector 8, but these connections may be inverted.

Either a direct current or an alternating current may be used for the high-tension power unit 7 for applying a high voltage to the hermetically sealed package 3 being conveyed, but a direct current has a lower-cost benefit because it does not require a rectifier.

To check whether there is a change in the electric current at the portion where the conductive element 5 contacts and the portion where at least one of the two longitudinally arranged conductive elements 6, 6 contacts when a high voltage is applied to the hermetically sealed package 3, a current transformer (CT) of a type that is used by winding its detecting part around the lead wire 9a or 9b through which the electric current flows, or in electric current detector that is directly connected to the lead wire 9a or 9b may be used. It is also possible to input the output from a current probe through which the lead wire 9a or 9b runs into an oscilloscope to detect a change in the electric current.

EXAMPLES

The drawings depict a case in which the hermetically sealed package 3 for inspection is a flat bag.

This bag 3 is made of a moderately thick plastic film 2 and has a cross section of approximately 130 mm (width)×180 mm (length)×12 m (height) and a volume of approximately 400 ml.

Each of the two longitudinally arranged conveyors 4, 4 for conveying this bag 3 consists of an endless belt 4a of a width slightly wider than 160 mm, which is capable of conveying the bag 3 in a stable manner. The belt 4a has a thickness of approximately 1 mm. The endless belt 4a is hung on a pair of longitudinally arranged rollers 4b, 4b each having a diameter of approximately 40 mm. In order to allow the conductive element 5 to approach from one side of the path A, the conveyors 4, 4 are set apart by approximately 35 mm.

In FIG. 1, in order to make, the two longitudinally arranged conveyors 4, 4 run in the same direction at the same speed, the rear roller 4b of the downstream conveyor 4 and the front roller 4b of the upstream conveyor 4 are driven by an endless driving belt 4c. When one of the rollers 4b, 4b (e.g., the roller 4b of the downstream conveyor 4 in FIG. 1) is driven, the upstream conveyor 4 and the downstream conveyor 4 run at the same speed in the same direction (indicated by the arrows pointing at the left-hand side of the drawing).

The conductive element 5, which approaches the path A from one side of the path A, and the conductive elements 6, 6, which approach the path A from the other side, so as to respectively touch a opposing surfaces of the contents 1—existing portion of the hermetically sealed package 3 conveyed on the conveyors 4, 4, have the following dimensions.

The supporting members 5b, 6b have a height of approximately 20 mm, the brushes 5a, 6a projecting from the supporting members 5b, 6b have a height of approximately 25 mm, and the supporting pedestals 5c, 6c have a peak height of approximately 55 mm. They all have a width of approximately 160 mm (in the direction that runs perpendicular to the surface of the paper on which FIG. 1 is drawn). Because the brushes 5a, 6a have a width of approximately 160 mm, their tips can touch the entire areas of the opposing surfaces of the contents 1—existing portion, which are within the flat surfaces having a width of approximately 130 mm of the hermetically sealed package 3 being conveyed on the two longitudinally arranged conveyors 4, 4.

In the example shown in the drawings, the two longitudinally arranged conductive elements 6, 6 are arranged to approach the path A from above. In this example, they are hung using the supporting members 6d, 6d.

The procedure for inspecting whether there is a pinhole on at least one of the opposing surfaces of the contents 1—existing portion of a hermetically sealed package 3 using the device depicted in FIG. 1 will now be explained by reference to FIG. 2.

Figure 2:
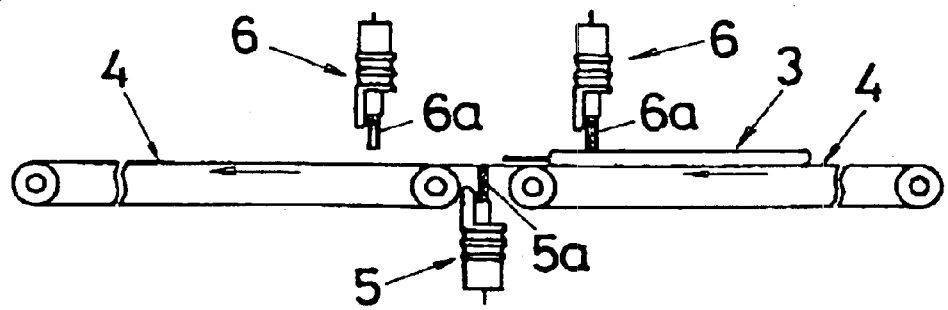
FIG. 2 is a process diagram showing a procedure for inspecting whether there is a pinhole on either of the opposing surfaces of the contents-containing portion of a hermetically sealed package using the device shown in FIG 1.
Figure 2:
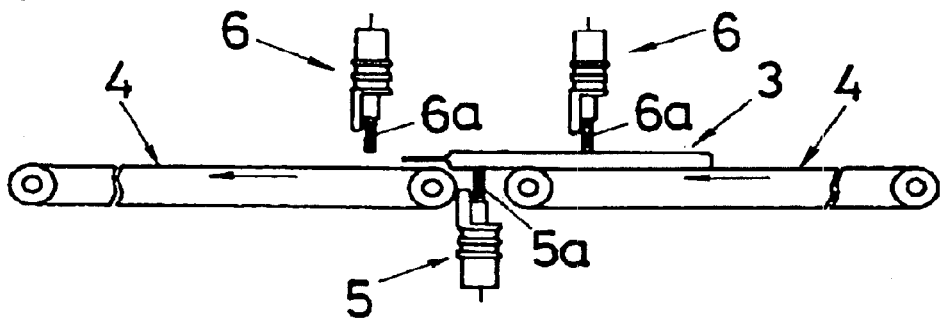
Figure 2:
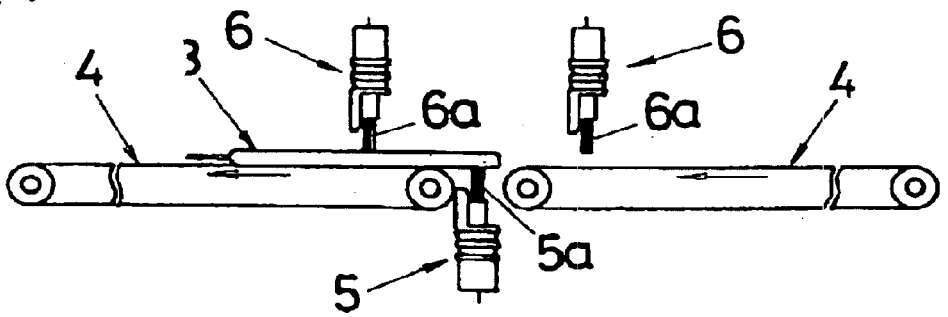
Figure 2:
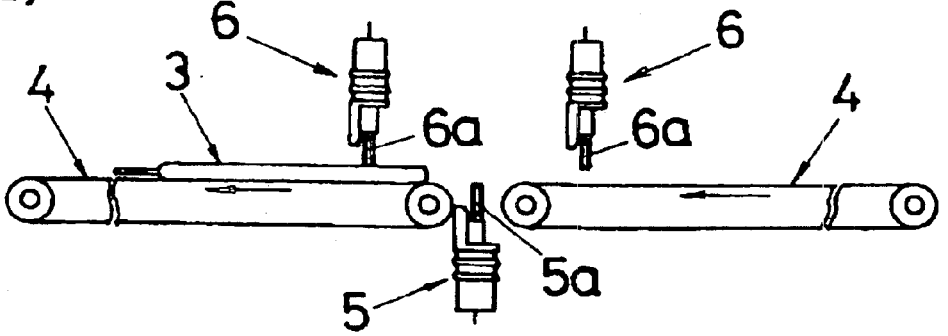

First, the upstream conveyor 4 and the downstream conveyor 4 are driven at the same speed in the same direction (i.e., the direction indicated by the arrows pointing at the left-hand side of FIG. 2). Then the brush 6a of the conductive element 6 on the upstream side of the two longitudinally arranged conductive elements 6, 6 contacts one surface (the upper surface in the drawing) of the hermetically sealed package 3 that has been carried over on the upstream conveyor 4, and the package will be conveyed forward with the tip of the brush 6a maintaining contact (see FIG. 2(a)).

When the hermetically sealed package 3 comes within the reach of the conductive element 5, which approaches the path A from one side of the two longitudinally arranged conveyors 4, 4, the brush 5a touches the other surface (lower surface in the drawing) of the hermetically sealed package 3 (see FIG. 2(b)). So far, only one surface of the package was touched by the brush 6a. This time, the brushes 6a and 5, which are on the opposite sides of the path A, touch the opposing surfaces (the upper and lower surfaces in the drawing) of the contents 1—existing portion of the hermetically sealed package 3 at the same time.

In this way, a high voltage from the high-tension power unit 7 can be applied to the hermetically sealed package 3 via the lead wire 9a. By using the electric current detector 8 to check whether there is a change in the electric current at the portion where the conductive element 5 contacts and the portion where at least one of the two longitudinally arranged conductive elements 6, 6 contacts, it can be checked easily whether there is a pinhole on any portion within the forward half range of the opposing surfaces of the contents 1—existing portion of the hermetically sealed package 3 in simultaneous inspections of both surfaces.

As the two longitudinally arranged conveyors 4, 4 continue to run, the hermetically sealed package 3 being conveyed transfers from the upstream conveyor 4 to the downstream conveyor 4, and moves on until it contacts the brush 6a of the downstream conductive element 6 of the two longitudinally arranged conductive elements 6, 6. The package keeps on moving forward (see FIG. 2(c)). At this time, the other surface (the lower surface in the drawing) of the hermetically sealed package 3 maintains contact with the brush 5a.

In this way, a high voltage can be applied from the high-tension power unit 7 to the hermetically sealed package 3 via the lead wire 9a. By using the electric current detector 8 to check whether there is a change in the electric current at the portion where tab conductive element 5 contacts and the portion where at least one of the two longitudinally arranged conductive elements 6, 6 contacts, it can be checked easily whether there is a pinhole on any portion within the rearward half range of the opposing surfaces of the contacts 1—existing portion of the hermetically sealed package 3 in simultaneous inspections of both surfaces.

While the hermetically sealed package 3 moves from the position depicted in FIG. 2(b) to that depicted in FIG. 2(c), all three brushes, i.e., the brush 5a of the conductive element 5 and the two brushes 6a, 6a of the conductive elements 6, 6 arranged on the other side, may contact the opposing surfaces of the contents 1—existing portion of the hermetically sealed package 3 at the same time. Even in this case, it is possible to check easily whether there is a pinhole in the opposing surfaces of the contents 1—existing portion of the hermetically sealed package 3 in the same manner in simultaneous inspections of both surfaces.

As the conveyors 4, 4 continue to run, the hermetically sealed package 3 being conveyed is further conveyed forward until the brush 5*a* of the conductive element 5 does not touch the surface (the lower surface in the drawing) of the hermetically sealed package 3 any more.

In this condition, the high voltage from the high-tension power unit 7 is no longer applied to the hermetically sealed package 3, and the inspection for pinholes is finished.

What is claimed is:

1. A device for inspecting relatively flat hermetically sealed packages (3), which wrap, with an electric insulating film, conductive contents (1), e.g., blood products, said device inspecting the entire areas of the opposing surfaces of the contents (1) of a hermetically sealed package (3) to check whether or not there is a pinhole on any portion of at least one of the opposing surfaces with conveying the hermetically sealed package (3), comprising:

two ungrounded conveyors (4, 4) for conveying a hermetically sealed package (3), which wraps, with an electric insulating film (2), conductive contents (1) such as blood products, etc.; said conveyors (4, 4) being arranged longitudinally with a distance between them over which the hermetically sealed package (3) can be transferred from one to the other;

a conductive element (5) provided to approach the path A from one side and between the two longitudinally arranged conveyors (4, 4);

two longitudinally provided conductive elements (6, 6) provided to approach the path A from an other side of the path A with a distance between said conductive element (6, 6) such that at least one of the conductive elements (6, 6) and the conductive element (5) simultaneously touch the opposing surfaces of the contents (1) of one hermetically sealed package (3) from the one and other sides of the path A;

a high-tension power unit (7) connected to either the conductive element (5) or the two longitudinally arranged conductive elements (6, 6); and an electric current detector (8) connected to one of the conductive element (5) and the two conductive elements (6, 6) which is not connected to the high-tension power unit (7) for checking whether there is a change in the electric current at the portion where the conductive element (5) contacts and the portion where at least one of the two longitudinally arranged conductive elements (6, 6) contacts.

2. The device according to claim 1 wherein the high-tension power unit (7) is an alternating current power unit.

* * * * *